US00PP27512P2

(12) United States Plant Patent
van der Velden

(10) Patent No.: US PP27,512 P2
(45) Date of Patent: Dec. 27, 2016

(54) ***TILLANDSIA* PLANT NAMED 'BIANCINI'**

(50) Latin Name: ***Tillandsia cyanea*×*Tillandsia pretiosa***
Varietal Denomination: Biancini

(71) Applicant: Josephus van der Velden, Sint-Oedenrode (NL)

(72) Inventor: Josephus van der Velden, Sint-Oedenrode (NL)

( * ) Notice: Subject to any disclaimer, the term of this patent is extended or adjusted under 35 U.S.C. 154(b) by 69 days.

(21) Appl. No.: 14/545,443

(22) Filed: May 5, 2015

(51) Int. Cl.
*A01H 5/02* (2006.01)

(52) U.S. Cl.
USPC ..... Plt./370

(58) Field of Classification Search
USPC ..... Plt./370
See application file for complete search history.

*Primary Examiner* — Anne Grunberg
(74) *Attorney, Agent, or Firm* — Penny J. Aguirre

(57) ABSTRACT

A new cultivar of *Tillandsia* named 'Biancini', that is characterized by its compact plant habit and its flowers and inflorescence bracts that are stably white in color.

2 Drawing Sheets

Botanical classification: *Tillandsia cyanea*×*Tillandsia pretiosa.*

Cultivar designation: 'Biancini'.

BACKGROUND OF THE INVENTION

The present invention relates to a new and distinct cultivar of *Tillandsia* plant of hybrid origin, botanically known as *Tillandsia* 'Biancini' and will be referred to hereafter by its cultivar name, 'Biancini'. 'Biancini' is grown as an indoor potted plant.

The new cultivar was developed through on ongoing breeding program conducted by the Inventor in Sint-Oedenrode, The Netherlands. 'Biancini' was derived from a cross made in April of 2008 between *Tillandsia cyanea* 'Anita' (not patented) as the female parent and an unnamed plant of *Tillandsia pretiosa* (not patented) as the male parent. 'Biancini' was selected as a single unique plant in March of 2011 from amongst the resulting seedlings.

Asexual propagation of the new cultivar was first accomplished by basal cuttings in Sint-Oedenrode, The Netherlands in April of 2011 by the Inventor. Asexual propagation by stem cuttings has determined that the characteristics of this cultivar are stable and are reproduced true to type in successive generations.

SUMMARY OF THE INVENTION

The following traits have been repeatedly observed and represent the characteristics of 'Biancini'. These attributes in combination distinguish 'Biancini' as a new and distinct cultivar of *Tillandsia.*

1. 'Biancini' exhibits a compact plant habit.
2. 'Biancini' exhibits flowers that are stably white in color.
3. 'Biancini' exhibits inflorescence bracts that are stably white in color.

The female parent of 'Biancini', 'Anita', differs from 'Biancini' in having inflorescence bracts that are deep pink in color and in having flowers that are purple in color. The male parent of 'Biancini' differs from 'Biancini' in having inflorescence bracts that are light pink to greenish white in color, in having flowers that are purple in color, in having a more vigorous growth habit, and a less compact plant habit. 'Biancini' can be most closely compared to the *Tillandsia cyanea* 'Josee' (U.S. Plant Pat. No. 20,014). 'Josee' is similar to 'Biancini' in having a compact plant habit. 'Josee' differs from 'Biancini' in having inflorescence bracts that are light pink in color; in having flowers that are light purple in color, and in having inflorescences that are branched.

BRIEF DESCRIPTION OF THE DRAWINGS

The accompanying colored photographs illustrate the overall appearance and distinct characteristics of the new *Tillandsia*. The photographs were taken of a 1 year-old plant of the new cultivar as grown in a 9-cm container in a heated glass greenhouse in Sint-Oedenrode, The Netherlands.

The photograph in FIG. 1 provides a side view of 'Biancini' in bloom.

Figure 1:
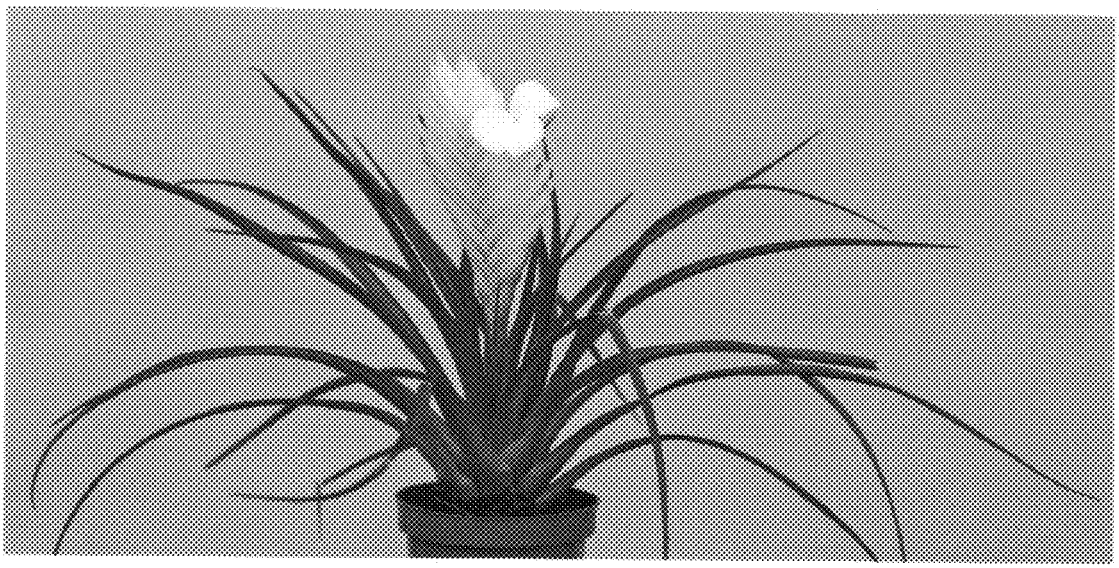
Figure 2:
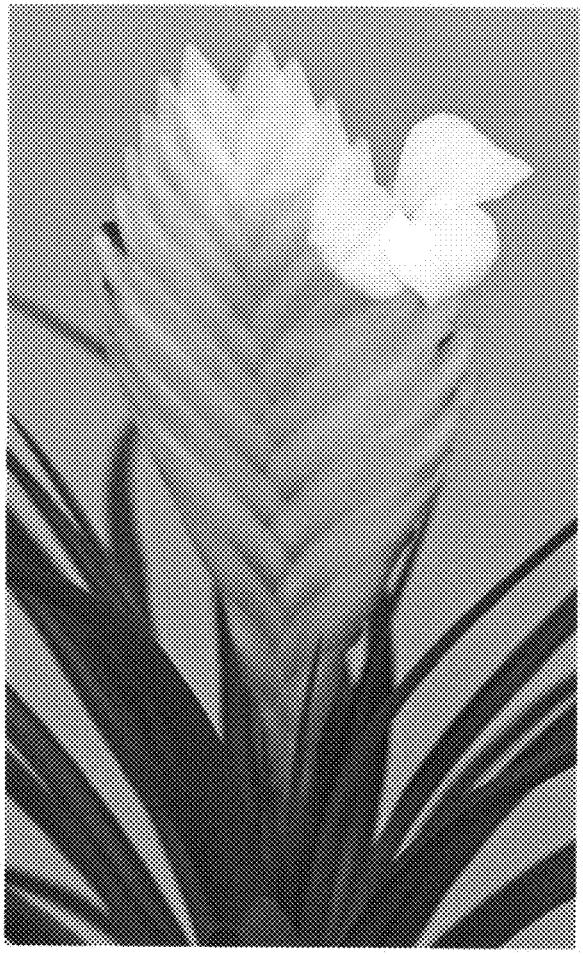

The photograph in FIG. 2 provides a close-up view of an inflorescence of 'Biancini'.

Figure 3:
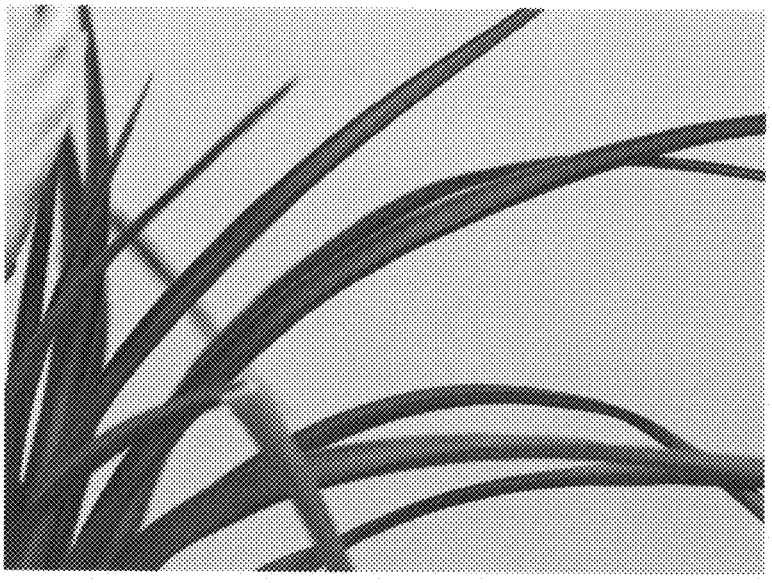

The photograph in FIG. 3 provides a close-up view of the foliage of 'Biancini'.

The colors in the photographs are as close as possible with the digital photography and printing techniques utilized and the color codes in the detailed botanical description accurately describe the new *Tillandsia.*

DETAILED BOTANICAL DESCRIPTION OF THE PLANT

The following is a detailed description of 1 year-old plants of the new cultivar as grown in 9-cm containers in a heated glass greenhouse in Sint-Oedenrode, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—Blooms for about 2 months in The Netherlands, any time of year one year from propagation.

*Plant type*.—Monocarpic.

*Plant habit*.—Compact, basal rosette, broad spreading, grass-like foliage.

*Height and spread*.—An average of 25 cm in height and 30 cm in spread.

*Hardiness*.—At least in U.S.D.A. Zone 10.

*Diseases and pests*.—No particular resistance and susceptibility to diseases and pests has been observed.

*Root description*.—Fine and fibrous roots.

*Propagation*.—Basal cuttings, one year is required to produce a blooming size plant.

*Growth rate*.—Moderately vigorous.

*Stem description*.—Basal rosette, no lateral branches present.

Foliage description:

*Leaf shape*.—Linear, carinate.

*Leaf division*.—Simple.

*Leaf base*.—Sheathing.

*Leaf apex*.—Long acuminate.

*Leaf venation*.—Parallel, color upper surface; N137B and lower surface; 137C with midrib a blend of 137D and 138A.

*Leaf margins*.—Entire.

*Leaf attachment*.—Decurrent, no petioles.

*Leaf arrangement*.—Rosulate, basal rosette.

*Leaf orientation*.—Held upright to broadly-spreading and arching downward.

*Leaf surface*.—Both surfaces glabrous and moderately glossy.

*Leaf color*.—Young and mature leaves upper surface; N137B and lower surface; 137C.

*Leaf size*.—An average of 26.5 cm in length and 6.5 mm in width.

*Leaf quantity*.—An average of 32 leaves per rosette.

*Leaf sheath*.—An average of 4.3 cm in length and 2.1 cm in width, color; 146B to 146C with base 161A to 161B.

Flower description:

*Inflorescence type*.—Terminal rhipidium with conduplicate bracts.

*Inflorescence size*.—An average of 13.5 cm in height and 3.4 to 7.5 cm in width.

*Lastingness of inflorescence*.—About 2 months, each flower lasts about one week, persistent.

*Flower size*.—An average of 6.5 cm in depth and 3.5 cm in diameter.

*Flower fragrance*.—Very faint, sweet scent.

*Flower shape*.—Single, monocarpous.

*Flower number*.—An average of 17 flowers per basal rosette.

*Flower aspect*.—Slightly outward at an average angle of 45° to vertical.

*Flower bud*.—Linear in shape, fully enclosed by bract, an average of 3.7 cm in length and 4 mm in width, 145B to 145C in color.

*Rate of flower opening*.—About 5% of flowers open at any time, flowers bloom all year long.

*Petals*.—3, spathulate in shape, rotate in arrangement, an average of 8.0 cm in length and 2.0 cm in width, entire margins, broadly acute apex, cuneate base, both surfaces glabrous, dull, and moderately velvety, color; upper and lower surface when opening and when fully open; lighter than NN155D, color fades to N88A.

*Sepals*.—3, rotate in arrangement, an average of 3.9 cm in length and 3 mm in width, narrow oblanceolate in shape, prominently carinate, entire margins, cuneate base, long acute apex, color; upper surface when opening 145D and lower surface 145C, upper surface when fully open; 145C and lower surface 145B to 145C, upper and lower surfaces; smooth and glossy.

*Calyx*.—Tubular, an average of 3.9 cm in length and 4 mm in diameter.

*Peduncle*.—An average of 8.4 cm in length and 4 mm in diameter, strong, held upright on plant (vertical), N144D in color.

*Bracts*.—Strongly carinate, ovate in shape, conduplicate, an average of 8 mm in width and 1.3 cm in length, entire margins, acute apex, sheathing base, color; upper and lower surfaces NN155D with base 144D, mature bracts on shady side fade to a blend between 145B to 145C and 147D.

Reproductive organs:

*Gynoecium*.—1 pistil, about 7 mm in length, style; about 5 mm in length, 150D in color, stigmas; three-lobed, club-shaped, 145D in color, ovary; 150C to 150D in color.

*Androecium*.—6 stamens, anthers; linear in shape, 5.5 mm in length and N144D in color; filament; 1.8 cm in length, 145A to 145B in color with NN155D at the base, pollen; high in quantity and 8A in color.

*Fruit/seeds*.—None observed.

It is claimed:

1. A new and distinct cultivar of *Tillandsia* plant named 'Biancini' as herein illustrated and described.

* * * * *